United States Patent [19]
Glennon et al.

[11] Patent Number: 5,919,794
[45] Date of Patent: Jul. 6, 1999

[54] METHODS OF USING PHARMACEUTICAL TETRAHYDROISOQUINOLINES

[75] Inventors: Richard A. Glennon, Richmond; Richard Young, Glen Allen, both of Va.

[73] Assignee: Virginia Commonwealth University, Richmond, Va.

[21] Appl. No.: 09/075,327

[22] Filed: May 11, 1998

[51] Int. Cl.⁶ ............................................. A61K 31/47
[52] U.S. Cl. .................... 514/307; 514/309; 514/310; 514/291
[58] Field of Search ..................... 514/307, 309, 514/310

[56] References Cited

U.S. PATENT DOCUMENTS

| | | |
|---|---|---|
| 4,622,329 | 11/1986 | Bernáth et al. . |
| 4,908,361 | 3/1990 | Martin et al. . |
| 5,118,690 | 6/1992 | Minchin et al. . |
| 5,187,165 | 2/1993 | Hamer et al. . |
| 5,236,934 | 8/1993 | VanAtten ................................ 514/307 |
| 5,519,034 | 5/1996 | Kozlik et al. . |
| 5,747,506 | 5/1998 | Naef ....................................... 514/307 |

*Primary Examiner*—James H. Reamer
*Attorney, Agent, or Firm*—Whitham, Curtis & Whitham

[57] ABSTRACT

Methods of using pharmaceutical tetrahydroisoquinoline compounds for learning and/or memory enhancement, and for treatment of dementia, cocaine dependence, depression, eating disorders, anxiety, or attention deficit disorder with hyperactivity (ADHD).

12 Claims, No Drawings

METHODS OF USING PHARMACEUTICAL TETRAHYDROISOQUINOLINES

DESCRIPTION

BACKGROUND OF THE INVENTION (1) Field of the Invention

The invention is generally related to methods of using pharmaceutical tetrahydroisoquinoline compounds for learning and/or memory enhancement, and for treatment of dementia, cocaine dependence, depression, antiappetite, anxiety, or attention deficit disorder with hyperactivity (ADHD).

(2) Background Information

Phenylalkylamines represent a common structural unit found in many therapeutic agents as well as in certain drugs of abuse. For example, depending upon the presence and location of certain substituent groups, phenylalkylamines might possess central stimulant, hallucinogenic, or designer drug-like activities. Structure A below is the phenylalkylamine central stimulant amphetamine (1-phenyl-2-aminopropane), structure B shows two representative phenylalkyl-amine hallucinogens (viz., 1-[2,5-dimethoxy-4-X)-phenyl] -2-aminopropane which is DOM where X=methyl and DOB where X=bromo), structure C shows the phenylalkylamine designer drug 1-[(3,4-methylene dioxy) phenyl]-2-[(N-methyl)amino]-propane (MDMA or "XTC"), and structure D shows the structurally related agent 1-[(3, 4-methylenedioxy)phenyl]-2-aminopropane (i.e., MDA) that possesses all three properties of compounds A, B and C.

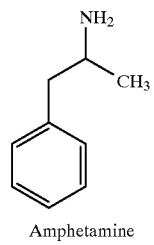

Amphetamine

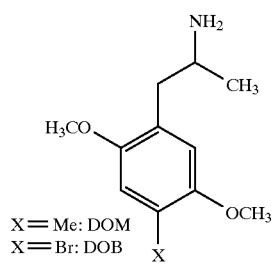

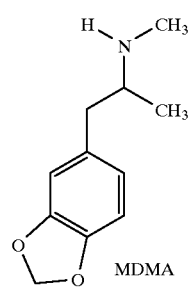

MDMA

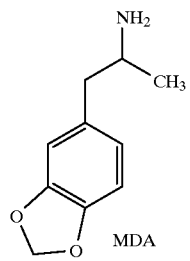

MDA

Studies of certain 1,2,3,4-tetrahydroisoquinolines and certain related analogs thereof, which might be considered as structurally restricted derivatives of A–D, for central stimulant and hallucinogenic effects associated with known phenylalkylamine hallucinogens, e.g., MDMA, or MDA, from a drug abuse and non-therapeutic perspective, have been previously reported. Malmusi, L. et al., *Med. Chem. Res.*, 1996, 6, 400–411; Malmusi, L. et al., *Med. Chem. Res.*, 1996, 6, 412–426; Nakagawa et al., *Biol. Pharm. Bull.* 1993, 16, 579–582.

As other background information, U.S. Pat. No. 4,908, 361 teaches tetrahydroisoquino [2,1-c][1,3]benzodiazepines used for enhancing memory in a mammal. U.S. Pat. No. 5,519,034 teaches certain tetrahydroisoquinoline compounds for use as analgesics, and in the treatment of psychoses, Parkinson's disease, Lesch-Nyan syndrome, attention deficit disorder or cognitive impairment or in the relief of drug dependence or tardive dyskinesia. U.S. Pat. No. 5,118,690 teaches pharmaceutical tetrahydroisoquinolines for treating pain and/or CNS disorders (e.g., anxiety, epilepsy, muscle spasms, sleep disorders, dyskinesia, depression and/or psychoses) characterized in that the method uses a compound which acts selectively as an antagonist of gamma aminobutyric acid (GABA) at GABA autoreceptors relative to $GABA_A$ receptors. U.S. Pat. No. 5,187,165 teaches various derivatives of esorline and related compounds useful for enhancing cholinergic function, as antidepressants and as analgesic agents. U.S. Pat. No. 4,696,913 teaches peptides which are active on the central nervous system and have an action on the cholinergic system. U.S. Pat. No. 4,622,329 teaches 1-cyclohexyl-3-4-dihydroisoquinoline derivatives which are pharmaceutically active, and in particular show antispasm, analgesic, gastric acid secretion inhibiting, sedative and hypnotic activity and effectively reduce the alcoholic narcosis time.

BRIEF SUMMARY OF THE INVENTION

This present invention relates to enhancing the learning and memory performance of an animal by administration to the animal of a therapeutically effective amount of tetrahydroisoquinoline compounds of formula I:

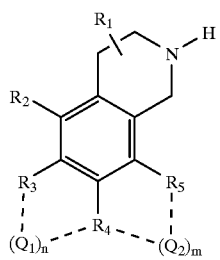

where $R_1$ is H or a lower alkyl group; $Q_1$ and $Q_2$ each represent an alkylene group, and n equals 0 or 1 and m equals 0 or 1; $R_2$, $R_3$, $R_4$ and $R_5$ are each independently chosen from among hydrogen, lower alkyl, lower alkoxy, hydroxy, nitro, carboxy, lower alkylthio, SH, amino, alkylamino, or halo, with the proviso that both $R_3$ and $R_4$, or both $R_4$ and $R_5$, alternatively may represent oxygen atoms when n equals 1 or m equals 1, respectively, with the further proviso that n and m cannot both simultaneously have a value of 1, and where the dotted lines represent bonds completing a 6,7-alkylenedioxy ring or 7,8-alkylenedioxy ring when n equals 1 or m equals 1, respectively; and pharmaceutically acceptable salts thereof.

One noteworthy effect of the usage of the compounds of formula I for eliciting enhanced learning and memory in an animal is the remarkable speed at which the animals treated with a formula I compound learn a lever response (for example, one week for compound Ie). In view of the fact that the compounds of formula I are effective to enhance learning and improve memory performance of the host or patient animal, they can be used in treatment of dementia, Alzheimer's Disease or other neurological impairments, damage, or disease causing memory decay and/or learning disabilities. In that regard, the compounds of formula I can be used to restore proper memory function.

An important advantage associated with the use of the compounds of formula I for enhancing learning and memory performance, or treating deficits thereof, is that the desired targeted therapeutic effect is achieved without causing the host/patient to suffer undesirable side effects such as inducing central nervous system stimulation, hallucinogenic effects, or a drug addiction thereto (as is the case for compounds A–D described in the Background Information section above).

This invention also relates to usage of the aforesaid tetrahydroisoquinoline compounds of formula I for effectively treating cocaine dependence, depression, antiappetite, anxiety, or attention deficit disorder with hyperactivity (ADHD).

The unique memory and learning-enhancing activities of tetrahydroisoquinoline compounds of this invention have been experimentally established and confirmed by studies that are described in the examples herein.

For purposes of this invention, the terminology "lower" used in connection with the definitions herein of formula I, means a group containing 1–6 carbon atoms, preferably 1–4 carbon atoms. The terminology "learning capability", as used herein, refers to the appropriateness and/or speed of a response for which a host or patient treated with a compound of formula I delivers in response to a given stimulus. The terminology "memory", as used herein, refers to the mental recollection of that which was previously experienced or learned by a host or patient having been treated with a compound of formula I.

DETAILED DESCRIPTION OF THE PREFERRED EMBODIMENTS OF THE INVENTION

In one implementation, the present invention relates to enhancing existing and/or restoring deficits in learning and memory capabilities in a host animal subject or patient with tetrahydroisoquinoline compounds of formula I defined as:

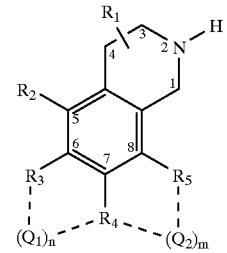

where $R_1$ is a hydrogen or lower alkyl group (e.g., such as methyl, ethyl, n-propyl, isopropyl, or n-butyl); $Q_1$ and $Q_2$ each can represent an alkylene group (e.g., methylenedioxy or ethylenedioxy); and n equals 0 or 1 and m equals 0 or 1; $R_2$, $R_3$, $R_4$ and $R_5$ are each independently chosen from among hydrogen, lower alkyl (e.g., methyl, ethyl, i-propyl, n-propyl), lower alkoxy (e.g., methoxy, ethoxy, propoxy), hydroxy, nitro, carboxy, lower alkylthio, SH, amino, alkylamino, or halo (e.g., bromo, fluoro, or chloro), with the proviso that both $R_3$ and $R_4$, or both $R_4$ and $R_5$, alternatively may represent oxygen atoms when n equals 1 or m equals 1, respectively, with the further proviso that n and m cannot both simultaneously have a value of 1, where the dotted lines represent bonds completing a 6,7-alkylenedioxy ring or 7,8-alkylenedioxy ring when n equals 1 or m equals 1, respectively; and pharmaceutically acceptable salts thereof.

The optional substitutions, $R_1$–$R_5$, indicated for the benzene ring and/or tetrahydropyrido ring of the formula I structure can be accomplished by conventionally known methodology, such as by techniques described in U.S. Pat. No. 5,118,690 or the above-cited Malmusi et al. publications, which teachings are incorporated herein by reference. However, the >N—H group at the number 2 position of the formula I compounds should not be substituted. For example, methylation of the nitrogen at the number 2 position of the ring renders the tetrahydroisoquinoline compound inactive for learning and memory improvement.

Several representative chemical structures of tetrahydroisoquinoline compounds within the scope of formula I are shown below as structures Ia–Ih:

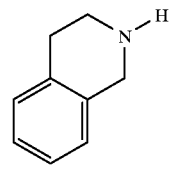

Ib
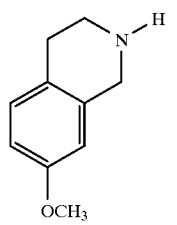

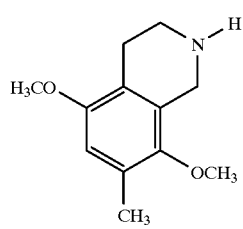
Ic

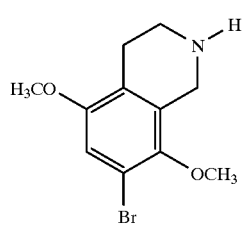
Id

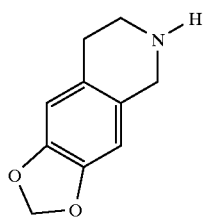
Ie

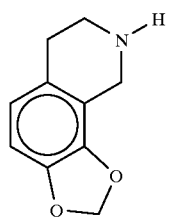
If

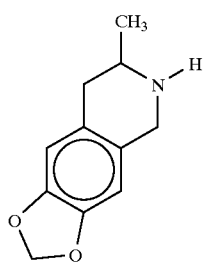
Ig

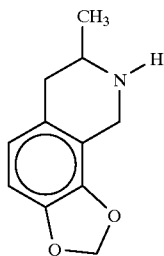
Ih

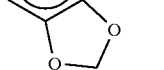

Compound Ia is 1,2,3,4,-tetrahydroisoquinoline. Compound Ib is 7-methoxy-1,2,3,4,-tetrahydroisoquinoline. Compound Ic is 5,8-dimethoxy-7-methyl-1,2,3,4,-tetrahydroisoquinoline. Compound Id is 5,8-dimethoxy-7-bromo-1,2,3,4,-tetrahydroisoquinoline. Compound Ie is 6,7-methylenedioxy-1,2,3,4,-tetrahydroisoquinoline. Compound If is 7,8-methylenedioxy-1,2,3,4,-tetrahydroisoquinoline. Compound Ig is 3-methyl-6,7-methylenedioxy-1,2,3,4,-tetrahydroisoquinoline. Compound Ih is 3-methyl-7,8-methylenedioxy-1,2,3,4,-tetrahydroisoquinoline.

It is understood that throughout the specification and the appended claims, a given chemical formula, viz., formula I, or chemical name shall encompass all stereo, optical, and geometrical isomers thereof where such isomers exist.

Compound Ie is one preferred compound of the present invention. Animals treated with compound Ie will learn and acquire a training stimulus in a drug discrimination assay more quickly as compared to an untreated animal or an animal treated with comparative previously reported training drugs such as amphetamine (Compound A), DOM (Compound B, X=methyl), and MDMA (Compound C).

Moreover, compound Ie is free of undesirable side effects otherwise associated with central stimulant phenylalkylamine drugs such as amphetamine or methylphenidate. Specifically, compound Ie does not produce locomotor stimulation in animals such as mice (a primary measure of central stimulation), nor is it recognized by amphetamine-trained animals in tests of stimulus generalization, and compound Ie-trained animals (e.g., rats) fail to recognize the stimulants amphetamine or methylphenidate.

Additionally, compound Ie is not a serotonin-like agent hallucinogenic agent in that it does not bind at 5-$HT_2$ receptors and it is not recognized by DOM-trained animals.

Also, compound Ie shares some stimulus actions similar to cocaine and MDMA, and, in experimental studies performed by the inventors, compound Ie-trained animals recognize cocaine and partially recognize MDMA. However, compound Ie lacks central stimulant activity so its potential for abuse is low, and its stimulus effects (unlike those of cocaine) are not antagonized by dopaminergic antagonists (e.g., a Di antagonist) or haloperidol. Consequently, it is surmised at this time that compound Ie might have psychotherapeutic potential, such as in cocaine-management therapy, treatment of ADHD, or treatment of depression or depressive disorders.

Pharmaceutical compositions used in the practice of the present invention can use one or a combination of different compounds within the scope of formula I, as described herein. Pharmaceutical compositions used in the practice of the present invention can be used with suitable pharmaceutically acceptable carriers.

The compounds of formula I can be used in free base form or, more preferably, they may be formulated and administered in the form of their pharmaceutically acceptable acid addition salts. Acids useful for preparing the pharmaceutically acceptable salts of the compounds of formula I include HCl, HBr, sulfuric, nitric, phosphoric, tartaric, citric, acetic, succinic, malic, fumaric, oxalic acids, and so forth.

Effective quantities of the compounds of formula I used in the practice of the invention may be administered to a patient by any of various methods, for example, orally, parenterally, nasally (e.g., aerosol), by transdermal patch, or by suppository.

The active compounds of formula I may be administered orally with an inert diluent or with an edible carrier. For oral administration, the compounds of formula I can be formulated and mixed with additives usual for this purpose, such as excipients, binders, carriers, fillers, stabilizers, lubricants, flavoring agents, preservatives, dyes, and so forth, and then are brought into suitable forms of administration, such as gelatin capsules, compressed tablets, coated tablets, aqueous alcoholic or oily suspensions, solutions, syrups, elixirs, and so forth.

Where the tetrahydroisoquinoline compounds of formula I are adapted for parenteral administration, such as intravenous or subcutaneous administration, the tetrahydroisoquinoline compounds may be dissolved, suspended or emulsified, if desired, with substances customary for that purpose, including suitable carrier liquids such as physiological saline, buffered saline, alcohols, sugar solutions, distilled water, fixed oils, alkylene glycols (e.g., polyethylene glycol, propylene glycol), glycerine, and so forth. The parenteral preparation can be enclosed in ampules, disposable syringes, or multiple dose vials made of plastic or glass.

Where the pharmaceutical compositions contemplated by this invention are intended for intravenous administration, the tetrahydroisoquinoline compounds preferably are introduced in solution form. Where the tetrahydroisoquinoline compounds described herein are intended for intramuscular or subcutaneous administration, they preferably are administered in either solution or suspension form.

The pharmaceutical compositions including the tetrahydroisoquinoline agents of formula I according to this invention can include such pharmaceutically acceptable additives or adjuncts to the extent that they do not hinder or interfere with the particular therapeutic effect desired of the tetrahydroisoquinoline compounds.

Preferred preparations used in the invention for oral administration to enhance learning/memory capabilities of an animal can be prepared to provide an oral dosage unit containing between 0.1 to 10 mg formula I compound/kg host or patient/24 hr.

For parenteral administration in an animal to enhance its learning/memory capabilities, a generally effective dosage ranges from about 0.1 to about 10 mg formula I compound/kg body weight/24 hr.

For oral administration in humans for treatment of cocaine dependence, depression, eating disorders such as hyperorexia, anxiety, or attention deficit disorder with hyperactivity (ADHD), a generally effective dosage ranges from about from about 0.1 to about 10 mg formula I compound/kg body weight/24 hr.

The administration of pharmaceutical compositions used in the present invention can be intermittent, or at a gradual, or continuous, constant or controlled rate to a warm-blooded animal. In addition, the time of day and the number of times per day that the pharmaceutical formulation is administered can vary. The level of efficacy and optimal amount of dosage for any given tetrahydroisoquinoline within the scope of formula I can vary one from the other depending on the type of animal host/patient and the type of treatment involved.

The host or patient for the therapeutic treatment using the tetrahydroisoquinoline compounds of formula I described herein generally are mammalian, such as humans, dogs, rodents, horses, apes, and so forth. Again, the effective dose can vary, depending upon factors such as the condition of the patient, the extent of the memory/learning deficit/decay being addressed or the severity of the affliction being treated, and the manner in which the pharmaceutical composition is administered.

In the following examples, objects and advantages of this invention are further illustrated by various embodiments thereof but the details of those examples should not be construed to unduly limit this invention.

All parts and percentages in the examples are by weight unless otherwise indicated.

EXAMPLES

Example 1

The drug discrimination studies used established and commonly employed procedures, such as described in: Glennon, Jarbe and Frankenheim, editors, *Drug Discrimination: Applications to Drug Abuse Research;* NIDA Monograph 116, U.S. Department of Health and Human Services, 1991, which descriptions are incorporated herein by reference. Several groups of rats were trained to recognize (i.e., discriminate) one of several agents from saline vehicle in standard two-lever operant chambers using a Vl 15 sec schedule of reinforcement for food reward such that they responded on the drug appropriate lever when administered the training drug (i.e., drug-appropriate responding) or on the vehicle-appropriate lever when administered vehicle (i.e., vehicle-appropriate responding). The training drugs included the stimulant (+)amphetamine (compound A), the hallucinogen DOM (compound B where X=Me), and the designer drug MDMA (compound C). Once training was complete (two to six months depending on the particular training drug) tests of stimulus generalization were conducted. That is, novel agents could be administered to these trained animals in order to determine whether or not the novel agent produces stimulus effects similar to those produced by one of the training drugs. For example, animals trained to discriminate (+)amphetamine from vehicle recognize other stimulants such as methamphetamine, but not hallucinogens such as DOM, whereas animals trained to discriminate the hallucinogen DOM recognize DOB (compound B where X=Br) but not the stimulants amphetamine or methamphetamine. In these tests, novel agents were administered to the animals in a dose-related fashion (one dose per week) in order to determine if they are recognized by one of the trained groups; this is determined by monitoring the animals drug-appropriate and vehicle-appropriate responding after administration of the novel agent. Animals were placed in the operant chambers for a maximum of 15 min per day and were tested on a daily basis. Animals received one intraperitoneal injection of drug per day. Each animal serves as its own control by comparing the test results with the animals response under the training drug and vehicle conditions from the prior days of that week. In like manner, a group of animals was also trained to discriminate Ie from vehicle.

Different types of results can be obtained from such studies (see Table 1). For example, (i) when the test drug produces effects similar to a training drug, stimulus generalization (G in Table 1) is said to have occurred; (ii) when the test drug produces effects that are unlike those produced by a training drug, vehicle-appropriate responding or no generalization (NG in Table 1) is said to have occurred. Intermediate results (i.e., results that are less than generalization but greater than no generalization) are difficult to interpret; this partial generalization (PG in Table 1) suggests that two agents may share some stimulus similarity but are clearly not identical.

More specifically, the various agents listed in Table 1 below were examined in 47 rats previously trained to discriminate either amphetamine (Compound A), DOM (Compound B, X=methyl), MDMA (Compound C), or Compound Ie, in the manner described above.

In the procedure, the 47 rats were trained to recognize the effect of a given agent (i.e., the training drug) and to respond accordingly in the manner describe above. Once the animals were trained to recognize a given agent, different agents were administered to the animals to determine if the animal recognized the new agent as producing stimulus effects similar to those produced by the training drug. This type of procedure is referred to as a test of stimulus generalization, and, in this manner, various agents can be classified as being amphetamine-like, DOM-like, or MDMA-like.

Results were qualitative and quantitative in that not only was it determined whether given drugs produced similar effects, but additionally the relative potencies of the various tested agents were determinable.

The results of the stimulus generalization studies using the 47 rats trained to discriminate either the active agent compound within the scope of the indicated tested formula I or the other indicated phenylalkylamines from saline vehicle, are set forth in Table 1 below. The various indicated compounds in Table 1 are defined hereinabove.

TABLE 1

| Test Agent | Comp. A | Training Drug Comp. B (X = Me) | Comp. C | Comp. Ie |
|---|---|---|---|---|
| Ia[i] | PG[2] | NG[3] | NG | G[1] |
| E1[ii] | NG | NG | NG | NG |
| Ie[iii] | NG | NG | PG | G |
| If | NG | NG | NG | G |
| Ig | NG | NG | NG | G |
| Ic | — | NG | NG | G |
| Ih | NG | NG | NG | G |
| Ib | NG | NG | G | G |
| Id | — | NG | NG | G |
| E2[iv] | — | NG | NG | NG |

[1]: G = generalization (i.e., similarity of effect)
[2]: PG = partial generalization
[3]: NG = no generalization (i.e., no similarity of effect)
[i]: produced 46% drug-appropriate responding in amphetamine-trained animals
[ii]: a comparison compound; 1,2,3,4,-tetrahydro-2-[N-methyl]-isoquinoline
[iii]: produced 75% MDMA-appropriate responding in MDMA-trained animals.
[iv]: a comparison compound; 5,8-dimethoxy-7-methyl-1,2,3,4,-tetrahydro-2-[N-methyl]-isoquinoline The results in Table 1 show that the tetrahydroisoquinoline compounds of formula I are generally devoid of the actions associated with their conformationally flexible analogs (i.e., Compounds A–D) with several limited exceptions noted below. For example, Compound Ia exhibits some amphetamine-like effects, but clearly fails to result in stimulus generalization. Likewise, compound Ie produced some MDMA-like effects, but not amphetamine-like or like effects. That is, Compound Ie, in particular, was found to produce some MDMA-like effects, in that compound Ie-trained rats recognized MDMA; on the other hand, the compound Ie-trained rats did not recognize the central stimulant Compound A or the hallucinogenic Compound B. This indicates that compound Ie has potential as a psychotherapeutic drug as it has partial similarity in effects with MDMA with lessened risk of drug abuse potential. Compound Ib produced MDMA-appropriate responding.

Compound Ia was found to be active in rats at ED50=1.5 mg/kg)(i.e., produces Ie-appropriate responding in Ie-trained animals). Compounds Ib and Ih were found to be active in rats at ED50=1.6 mg/kg). Compounds Ie and Ig were found to be active in rats at ED50=3.7 mg/kg. Compounds Ic and Id (ED50=4.2 and 3.1 mg/kg, respectively) were recognized by the animals trained with compound Ie. Compound If (ED=2.7 mg/kg) was found to produce compound Ie-like stimulus effect in Compound Ie-trained animals.

A group of rats were trained to discriminate compound Ie from vehicle and administered doses of amphetamine (Compound A) and DOM (Compound B, X=methyl) in the manner described above.

Neither the Compound A nor Compound B agent was recognized by the Compound Ie-trained animals.

Administration of MDMA (Compound C), however, resulted in partial generalization.

Administration of compound If (ED50=2.7 mg/kg) to the compound Ie-trained rats, in the manner described above, resulted in stimulus generalization.

Comparison Compound C1 and Compound C2 were found to be inactive.

It is apparent from the results that the presence of the formula I compound provided a significant improvement in the ability of the treated animals to learn.

While the invention has been described in terms of its preferred embodiments, those skilled in the art will recognize that the invention can be practiced with modification within the spirit and scope of the appended claims.

We claim:

1. A method of enhancing the learning capability and/or memory of an animal, comprising administering to a animal an effective learning and/or memory enhancing dose of a compound having the formula I:

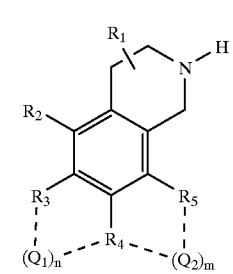

where $R_1$ is a lower alkyl group; $Q_1$ and $Q_2$ each represent an alkylene group, and n equals 0 or 1 and m equals 0 or 1; $R_2$, $R_3$, $R_4$ and $R_5$ are each independently chosen from among hydrogen, lower alkyl, lower alkoxy, hydroxy, nitro, carboxy, lower alkylthio, SH, amino, alkylamino, or halo, with the proviso that both $R_3$ and $R_4$, or both $R_4$ and $R_5$, alternatively may represent oxygen atoms when n equals 1 or m equals 1, respectively, with the further proviso that n and m cannot both simultaneously have a value of 1, and where the dotted lines represent bonds completing a 6,7-alkylenedioxy ring or 7,8-alkylenedioxy ring when n equals 1 or m equals 1, respectively; and pharmaceutically acceptable salts thereof.

2. The method of claim 1, wherein said compound is 6,7-methylenedioxy-1,2,3,4,-tetrahydroisoquinoline.

3. The method of claim 1, wherein said animal is a mammal.

4. The method of claim 1, wherein said animal is selected from the group consisting of a rodent, dog, and horse.

5. The method of claim 1, wherein said effective dose of said compound ranges from about 0.1 mg compound/kg body weight/24 hr. to about 10 mg/kg body weight/24 hr.

6. The method of claim 3, wherein said mammal is human.

7. The method of claim 1, wherein said step of administration is performed orally.

8. The method of claim 1, wherein said step of administration is performed parenterally.

9. The method of claim 1, wherein said step of administration is performed intravenously.

10. The method of claim 1, further comprising dispersing, dissolving or absorbing said compound of formula I in a pharmaceutically acceptable carrier prior to the step of administering to said mammal said effective dose of said compound.

11. A method of treating dementia in a human patient, comprising administering to a human afflicted with dementia an effective dose of a compound having the formula I:

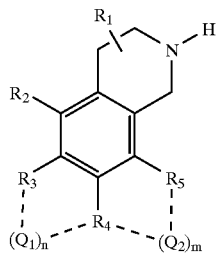

where $R_1$ is a lower alkyl group; $Q_1$ and $Q_2$ each represent an alkylene group, and n equals 0 or 1 and m equals 0 or 1; $R_2$, $R_3$, $R_4$ and $R_5$ are each independently chosen from among hydrogen, lower alkyl, lower alkoxy, hydroxy, nitro, carboxy, lower alkylthio, SH, amino, alkylamino, or halo, with the proviso that both $R_3$ and $R_4$, or both $R_4$ and $R_5$, alternatively may represent oxygen atoms when n equals 1 or m equals 1, respectively, with the further proviso that n and m cannot both simultaneously have a value of 1, and where the dotted lines represent bonds completing a 6,7-alkylenedioxy ring or 7,8-alkylenedioxy ring when n equals 1 or m equals 1, respectively; and pharmaceutically acceptable salts thereof.

12. A method of treating cocaine dependence, depression, eating disorder, anxiety, or attention deficit disorder with hyperactivity (ADHD) in an animal so afflicted, comprising administering to said animal so afflicted an effective amount of a compound having the formula I:

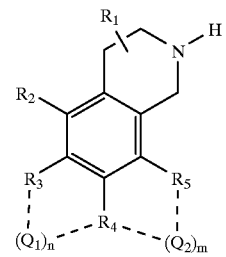

where $R_1$ is hydrogen or a lower alkyl group; $Q_1$ and $Q_2$ each represent an alkylene group, and n equals 0 or 1 and m equals 0 or 1; $R_2$, $R_3$, $R_4$ and $R_5$ are each independently chosen from among hydrogen, lower alkyl, lower alkoxy, hydroxy, nitro, carboxy, lower alkylthio, SH, amino, alkylamino, or halo, with the proviso that both $R_3$ and $R_4$, or both $R_4$ and $R_5$, alternatively may represent oxygen atoms when n equals 1 or m equals 1, respectively, with the further proviso that n and m cannot both simultaneously be equal to 1, and where the dotted lines represent bonds completing a 6,7-alkylenedioxy ring or 7,8-alkylenedioxy ring when n equals 1 or m equals 1, respectively; and pharmaceutically acceptable salts thereof.

* * * * *